US00PP29237P3

(12) United States Plant Patent
Koie et al.

(10) Patent No.: US PP29,237 P3
(45) Date of Patent: Apr. 17, 2018

(54) HOP PLANT NAMED 'FURANO 0802D GO'

(50) Latin Name: ***Humulus lupulus* L.**
Varietal Denomination: Furano 0802D go

(71) Applicant: Sapporo Breweries Limited, Tokyo (JP)

(72) Inventors: Koichiro Koie, Hokkaido (JP); Narushi Suda, Hokkaido (JP); Yutaka Itoga, Hokkaido (JP); Mitsuhiro Uemoto, Hokkaido (JP); Yasunori Arai, Hokkaido (JP); Masanobu Goto, Hokkaido (JP)

(73) Assignee: Sapporo Breweries Limited, Tokyo (JP)

( * ) Notice: Subject to any disclaimer, the term of this patent is extended or adjusted under 35 U.S.C. 154(b) by 0 days.

(21) Appl. No.: 14/757,381

(22) Filed: Dec. 21, 2015

(65) Prior Publication Data

US 2016/0192561 P1 Jun. 30, 2016

(30) Foreign Application Priority Data

Dec. 24, 2014 (JP) ..... 29811

(51) Int. Cl.
*A01H 5/02* (2018.01)

(52) U.S. Cl.
USPC ..... Plt./236
CPC ..... *A01H 5/02* (2013.01)

(58) Field of Classification Search
USPC ..... Plt./236
CPC ..... A01H 5/02; A01H 5/0825; A01H 5/0837
See application file for complete search history.

*Primary Examiner* — Kent L Bell
(74) *Attorney, Agent, or Firm* — James M. Weatherly; Bethany R. Roahrig; Cochran Freund & Young, LLC

(57) ABSTRACT

A new hop plant particularly distinguished by having a conical plant shape, alpha acid content of 4.2% in dry matter, a ratio content of beta to alpha of 1.1, a content of cohumulone to alpha acids of 48%, and a fruity, grape and citrus flavor, is disclosed.

2 Drawing Sheets

Genus and species: *Humulus lupulus* L.
Variety denomination: 'Furano 0802D go'.

CROSS REFERENCE TO RELATED APPLICATION

The present application claims priority to Japan Plant Variety Protection Application No. 29811, as filed on Dec. 24, 2014, the entire contents are herein incorporated by reference for all the application teaches and discloses.

BACKGROUND OF THE NEW PLANT

The present invention comprises a new and distinct variety of hop, botanically known as *Humulus lupulus* L. and hereinafter referred to by the variety name 'Furano 0802D go'. 'Furano 0802D go' is a selection from a controlled cross-pollination of the female hop parent 'USDA21055' and the proprietary male hop parent '020639'.

The female hop line 'USDA21055' and the proprietary male hop line '020639' were cross pollinated in Kamifurano, Hokkaido, Japan and seeds were obtained. The resulting seeds were sown and plants were grown for evaluation. A plant line was selected in March of 2008 in Kamifurano, Hokkaido, Japan and named 'Furano 0802D go'. In 2008, 'Furano 0802D go' was first vegetatively propagated by in Kamifurano, Hokkaido, Japan via vegetative cuttings. 'Furano 0802D go' was found to reproduce true to type in successive generations of asexual propagation via vegetative cuttings in Kamifurano, Hokkaido, Japan.

SUMMARY

The following are the most outstanding and distinguishing characteristics of this new variety when grown under normal horticultural practices in Kamifurano, Hokkaido, Japan.

1. Conical plant shape;
2. Alpha acid content of 4.2% in dry matter;
3. Ratio content of beta to alpha of 1.1;
4. Content of cohumulone to alpha acids of 48%; and
5. A fruity, grape and citrus flavor.

DESCRIPTION OF THE PHOTOGRAPHS

This hop plant is illustrated by the accompanying photographs which show the plant's overall plant shape, leaf shape and cone shape. The photographs are of six year-old plants grown in Kamifurano, Hokkaido, Japan in August 2014. The colors shown are as true as can be reasonably obtained by conventional photographic procedures.

Figure 1:
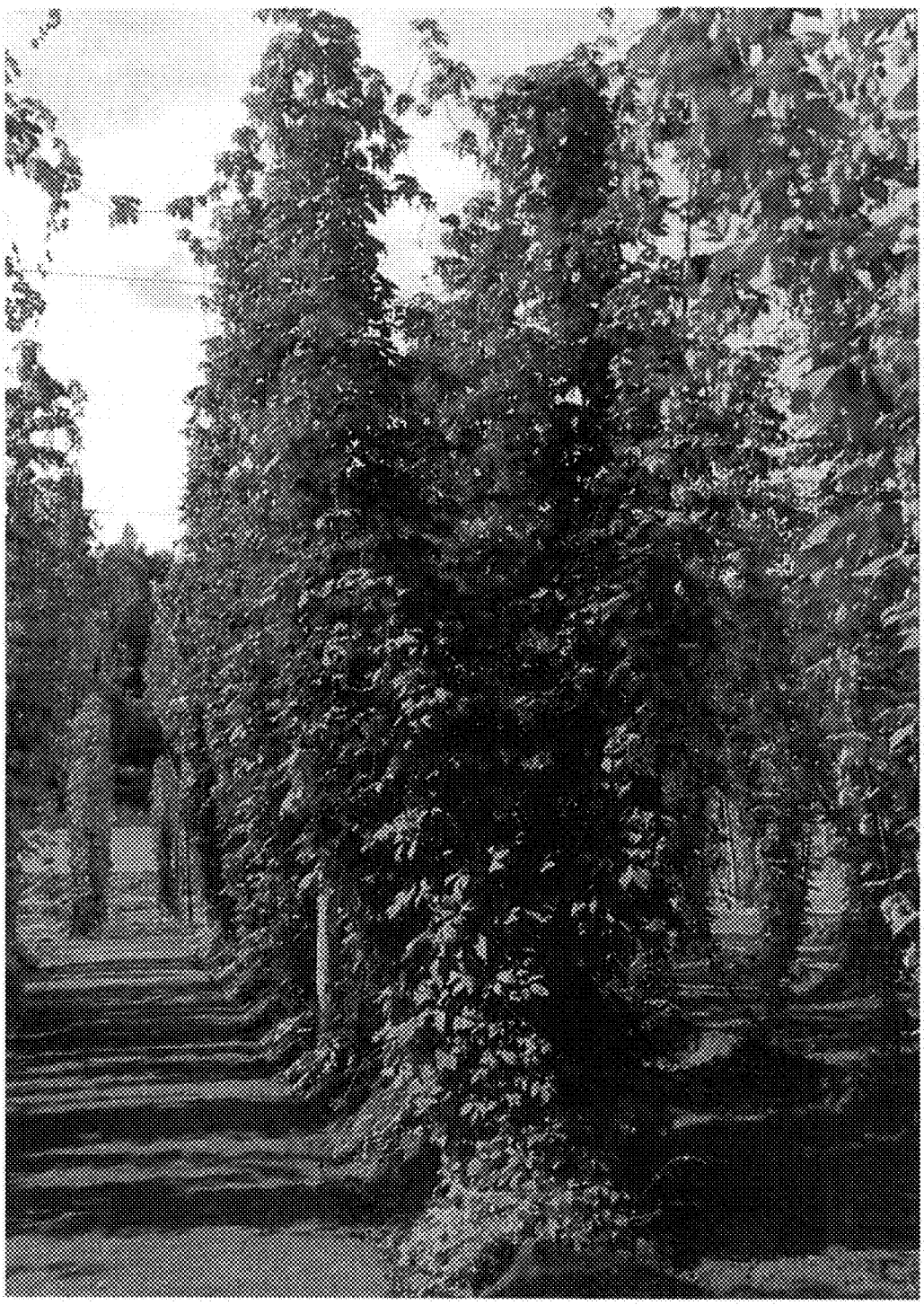

FIG. 1—Shows the plant shape of 'Furano 0802D go'.

Figure 2:
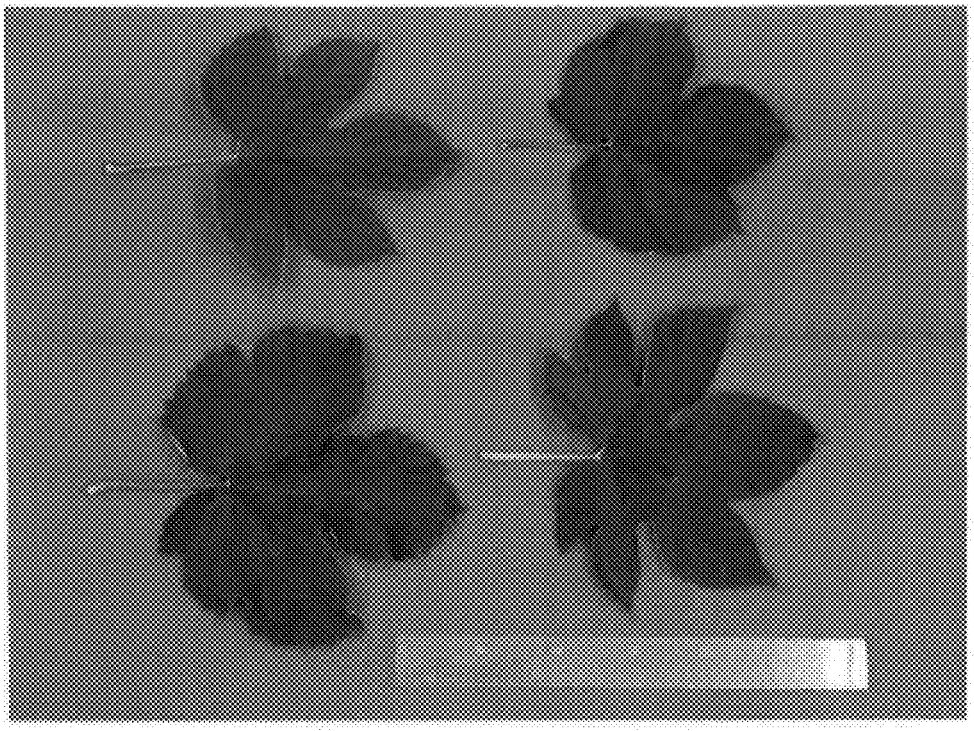

FIG. 2—Shows the leaf shape of 'Furano 0802 go' and three commercial hop varieties in Japan. On the lower right is 'Furano 0802D go'; in the upper right is 'Little Star'; in the upper left is 'Shinsyu Wase'; and in the lower left is 'Furano Special'.

Figure 3:
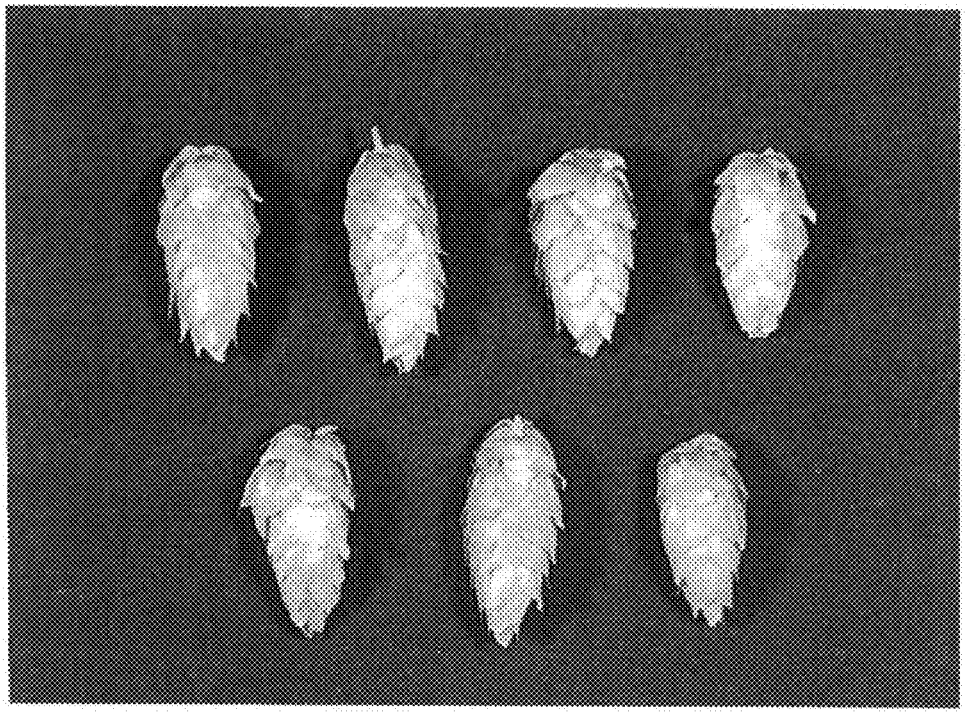

FIG. 3—Shows the cone shape of 'Furano 0802D go'.

DESCRIPTION OF THE NEW VARIETY

The following detailed descriptions set forth the distinctive characteristics of 'Furano 0802D go'. The data, which define these characteristics, were collected from asexual reproductions carried out in Kamifurano, Hokkaido, Japan. Data was collected on six- and seven-year-old plants in Kamifurano, Hokkaido, Japan during 2013 to 2017 growing seasons. Color references are to Japan Horticultural Plant Color Chart (1987, Japan Color Research Institute).

Classification:

*Family*.—Cannabaceae.

*Classification*.—*Humulus lupulus* L.

*Common name*.—Hop.

Propagation:

*Type*.—Vegetative Cuttings.

Plant description:

*Plant and growth habit*.—The plant growth type is normal, not dwarf.

*Plant height*.—5.5 m when grown on a trellis.

*Plant diameter*.—1.2 m to 1.5 m.

*Plant shape*.—Cylindrical.

Lateral branch description:

*Length*.—Average is 0.74 m.

*Diameter*.—Average is 3.8 mm; ranges between 3.2 mm and 4.4 mm.

*Internode length*.—Average 19.0 cm; ranges between 12.0 cm and 25.0 cm on the lateral branch at the middle of the plant.

*Color*.—Both the color of the ridge line and that of the area in-between are soft yellow green (Japan Color Chart No. 3310).

Foliage description:

*Arrangement*.—Opposite.

*Shape*.—7 lobes; sometimes the middle lobe is additionally lobed in 3.

*Length*.—Average is 17.1 cm; ranges between 14.0 cm and 20.0 cm.

*Width*.—Average is 20.6 cm (measured in 2016); ranges between 17.0 cm and 22.0 cm.

*Color*.—The leaf color of upper side is green (Japan Color Chart No. 3703).

*Apex*.—Accuminate to acute.

*Margin*.—Spiny.

*Base*.—Auriculate.

*Venation pattern*.—Palmate.

*Venation color*.—Dark yellowish green (Japan Color Chart No. 3508).

*Blistering*.—Upper surface: Weak.

*Petiole*.—Length: Average is 8.3 cm; ranges between 7.0 cm and 10.5 cm. Diameter: Average is 4.5 mm; ranges between 4.0 mm and 5.0 mm measured in the middle. Color: From base to bine is dull yellowish pink (Japan Color Chart No. 0711).

Inflorescence cones:

*Cone size*.—Small; Average length is 27.5 mm; ranges between 22.0 mm and 33.0 mm and average diameter is 12.6 mm; ranges between 11.0 mm and 14.0 mm.

*Cone shape*.—Narrow, ovate.

*Weight of hundred cones*.—13.8 g in dry matter.

*Color*.—Strong green yellow (Japan Color Chart No. 3311).

*Lupulin glands*.—Number per cone: Slightly more than normal. Shape: Round. Color: Bright yellow (Japan Color Chart No. 2506).

*Flowering date* (*the date when half of the plants are in bloom*).—July $6^{th}$.

*Harvest date*.—August 20th.

Bracts:

*Shape*.—Accuminate.

*Length*.—Average is 17.1 mm; ranges between 14.0 mm and 20.0 mm.

*Width*.—Average is 12.2 mm; ranges between 11.0 mm and 14.0 mm.

*Margin*.—Entire.

*Color*.—Dull yellow green (Japan Color Chart No. 3513).

Bracteoles:

*Shape*.—Orbicular to ovate.

*Length*.—Average is 8.9 mm; ranges between 6.5 mm and 11.0 mm.

*Width*.—Average is 6.6 mm; ranges between 4.5 mm and 8.5 mm.

*Apex*.—Round.

*Margin*.—Entire.

*Color*.—Pale yellow green (Japan Color Chart No. 3303).

Bines:

*Length*.—Greater than 5.5 m.

*Diameter*.—Average is 8.6 mm; ranges between 7.0 mm and 10.0 mm.

*Internode length*.—Average is 26.0 cm; ranges between 22.0 cm and 29.0 cm.

*Color*.—Soft yellow green (Japan Color Chart No. 3511).

*Anthocyanin coloration*.—Weak.

*Stipule number per bine*.—Equal to double the number of internodes.

*Stipule direction*.—Horizontal.

*Stipule color*.—Light yellow green (Japan Color Chart No. 3304).

Pedicels: Not observed.

Reproductive organs:

*Stamens*.—Not observed.

*Pistils*.—Not observed.

Yield: 1.11 tons/hectare (2014).

Disease and pest/insect resistance: None observed.

Brewing characteristics: Content of alpha acid is 4.2% in dry matter. Content of beta acids is 5.4% (data from 2013). Ratio content of beta to alpha is 1.1. Content of humulene is 5.9% (data from 2015). Content of caryophyllene is 7.0% (data from 2015). Ratio content of humulene to caryophyllene is 0.64 (data from 2015). Content of cohumulone to alpha acids is 48%. Content of myrcene is 73.3% (data from 2015). Content of farnesene is 9.2% (data from 2015). Content of linalool is 0.67% (data from 2015). Total oil: 1.80 mL per 100 g of cone weight. Flavor of 'Furano 0802D go' is fruity, such as grape and citrus. Storage stability: 80.1% after 6 months at room temperature (data from 2015).

COMPARISON WITH PARENTAL LINES AND KNOWN VARIETY

'Furano 0802D go' is a distinct variety of hop. 'Furano 0802D go' is distinguished from its female parent 'USDA21056' as described in Table 1:

TABLE 1

| Comparison with Parental Lines | | |
|---|---|---|
| Characteristic | Variety 'Furano 0802D go' | Female parent 'USDA21056' |
| Content of alpha acid in dry matter | 4.2% | 12.8% |
| Ratio content of beta acid to alpha acid | 1.1 | 0.6 |
| Content of cohumulone in alpha acid | 48% | 44% |

'Furano 0802D go' is distinguished from its male parent '020639' in that 'Furano 0802D go' develops female flowers that develop into mature hop cones without producing pollen, whereas '020639' produces pollen without developing into female flowers.

'Furano 0802D go' is distinguished from the commercial hop plant 'Little Star' (not patented). Differences between the two varieties are described in Table 2:

TABLE 2

| Comparison with Similar Variety | | |
|---|---|---|
| Characteristic | Variety 'Furano 0802D go' | Commercial line 'Little Star' |
| Flowering date | 6th July | 7th of July |
| Harvest date | 20th August | 21th August |
| Content of alpha acid in dry matter | 4.2% | 7.3% |
| Ratio content of beta acid to alpha acid | 1.1 | 0.7 |
| Content of cohumulone in alpha acid | 48% | 22% |

We claim:

1. A new and distinct variety of hop plant named 'Furano 0802D go' as illustrated and described herein.

* * * * *